(12) United States Patent
Osborne

(10) Patent No.: US 12,042,558 B2
(45) Date of Patent: *Jul. 23, 2024

(54) METHOD AND FORMULATION FOR IMPROVING ROFLUMILAST SKIN PENETRATION LAG TIME

(71) Applicant: ARCUTIS BIOTHERAPEUTICS, INC., Westlake Village, CA (US)

(72) Inventor: David W. Osborne, Fort Collins, CO (US)

(73) Assignee: ARCUTIS BIOTHERAPEUTICS, INC., Westlake Village, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/426,492

(22) Filed: May 30, 2019

(65) Prior Publication Data

US 2019/0365642 A1 Dec. 5, 2019

Related U.S. Application Data

(60) Provisional application No. 62/742,644, filed on Oct. 8, 2018, provisional application No. 62/680,203, filed on Jun. 4, 2018.

(51) Int. Cl.

| | |
|---|---|
| A61K 31/277 | (2006.01) |
| A61K 9/00 | (2006.01) |
| A61K 9/06 | (2006.01) |
| A61K 9/107 | (2006.01) |
| A61K 31/122 | (2006.01) |
| A61K 31/17 | (2006.01) |
| A61K 31/194 | (2006.01) |
| A61K 31/366 | (2006.01) |
| A61K 31/44 | (2006.01) |
| A61K 31/52 | (2006.01) |
| A61K 31/5377 | (2006.01) |
| A61K 31/573 | (2006.01) |
| A61K 31/60 | (2006.01) |
| A61K 47/10 | (2017.01) |
| A61K 47/14 | (2017.01) |
| A61K 47/24 | (2006.01) |
| A61K 47/69 | (2017.01) |
| A61P 17/06 | (2006.01) |
| A61K 45/06 | (2006.01) |

(52) U.S. Cl.
CPC .............. *A61K 9/0014* (2013.01); *A61K 9/06* (2013.01); *A61K 9/107* (2013.01); *A61K 31/122* (2013.01); *A61K 31/17* (2013.01); *A61K 31/194* (2013.01); *A61K 31/366* (2013.01); *A61K 31/44* (2013.01); *A61K 31/52* (2013.01); *A61K 31/5377* (2013.01); *A61K 31/573* (2013.01); *A61K 31/60* (2013.01); *A61K 47/10* (2013.01); *A61K 47/14* (2013.01); *A61K 47/24* (2013.01); *A61K 47/6903* (2017.08); *A61P 17/06* (2018.01); *A61K 45/06* (2013.01)

(58) Field of Classification Search
None
See application file for complete search history.

(56) References Cited

U.S. PATENT DOCUMENTS

| | | |
|---|---|---|
| 4,482,537 A | 11/1984 | El-Menshawy et al. |
| 5,374,661 A | 12/1994 | Betlach, II |
| 5,712,298 A | 1/1998 | Amschler |
| 5,863,560 A | 1/1999 | Osborne |
| 6,056,955 A | 5/2000 | Fischetti et al. |
| 6,060,085 A | 5/2000 | Osborne |
| 6,106,848 A | 8/2000 | Preuilh et al. |
| 6,117,915 A | 9/2000 | Pereira et al. |
| 6,214,322 B1 | 4/2001 | Castro et al. |
| 7,470,791 B2 | 12/2008 | Kohl et al. |
| 7,951,398 B2 | 5/2011 | Dietrich et al. |
| 8,293,288 B2 | 10/2012 | Ma |
| 8,338,648 B2 | 12/2012 | Stock et al. |
| 8,377,663 B2 | 2/2013 | Lintner et al. |
| 8,536,206 B2 | 9/2013 | Kohl et al. |
| 8,618,142 B2 | 12/2013 | Kohl et al. |
| 8,884,034 B2 | 11/2014 | Daynard et al. |
| 9,205,044 B2 | 12/2015 | Linder |
| 9,649,302 B2 | 5/2017 | Vakkalanka |

(Continued)

FOREIGN PATENT DOCUMENTS

| | | |
|---|---|---|
| CN | 1655782 | 8/2005 |
| CN | 101061993 A | 10/2007 |

(Continued)

OTHER PUBLICATIONS

Notification of Transmittal of the International Search Report and Written Opinion cited in PCT/US2019/034640, dated Dec. 4, 2019, 14 pages.
Final Office Action issued in U.S. Appl. No. 15/712,900 dated May 23, 2022, 14 pages.
ip.com translation KR 1999-0015251 A, printed 2022 (Year: 2022).
Chinese Patent Application No. 201880060842.2 dated Feb. 22, 2023, 13 pages.

(Continued)

*Primary Examiner* — Layla Soroush
(74) *Attorney, Agent, or Firm* — Rothwell, Figg, Ernst & Manbeck, P.C.

(57) ABSTRACT

Decreasing skin penetration lag times will improve the bioavailability of a topically administered roflumilast composition. A shorter skin penetration lag time provides quicker onset of disease relief and more consistent bioavailability as there is less transference to clothing or other people. The skin penetration lag time for roflumilast can be reduced by formulating a roflumilast composition to have a pH between 4.0-6.5 and/or combining roflumilast with an emulsifier blend comprising cetearyl alcohol, dicetyl phosphate and ceteth-10 phosphate.

6 Claims, 3 Drawing Sheets

(56) References Cited

U.S. PATENT DOCUMENTS

Figure 1:
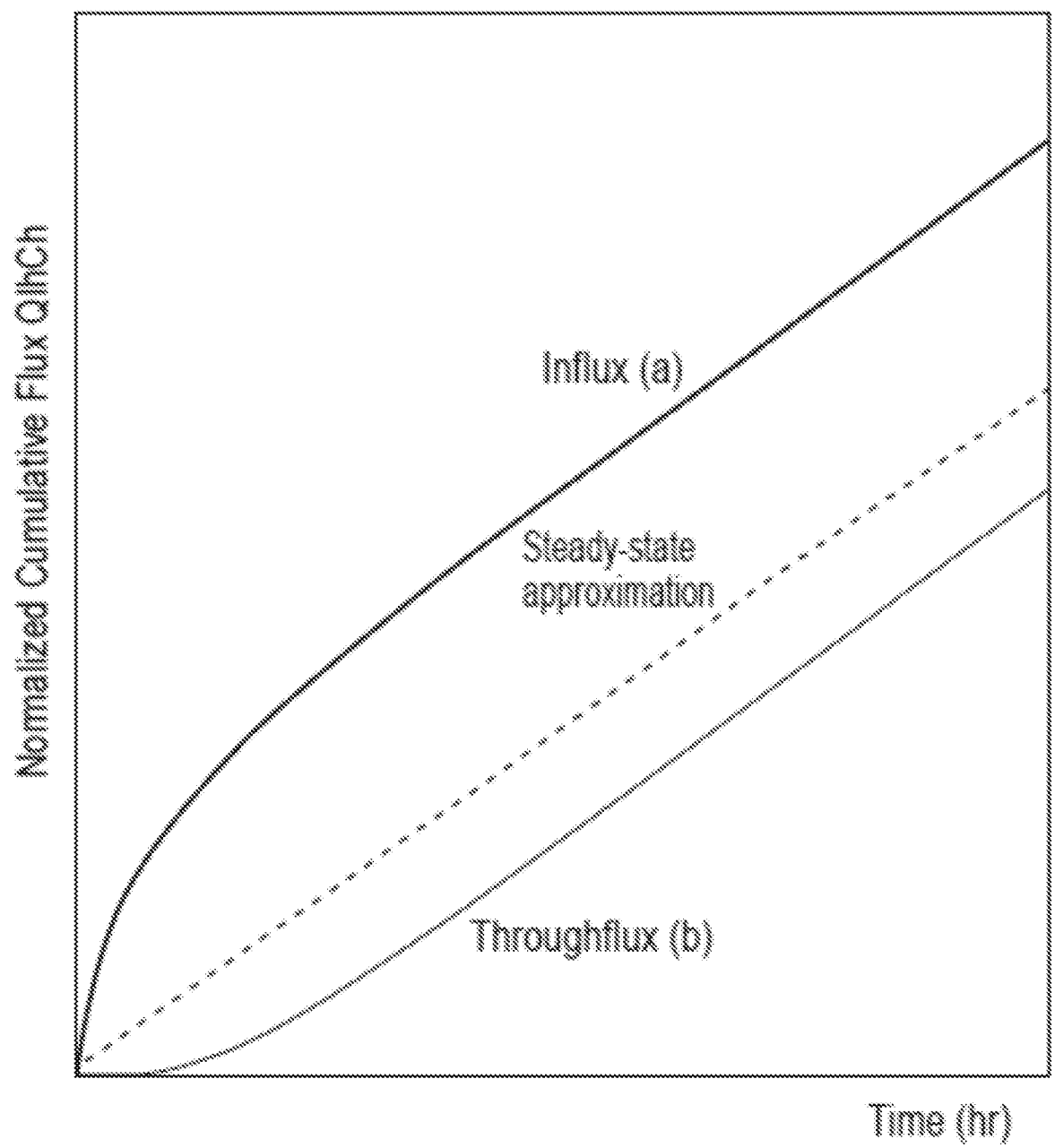

| | | | |
|---|---|---|---|
| 9,884,050 | B1 | 2/2018 | Osborne |
| 9,895,359 | B1 | 2/2018 | Osborne |
| 9,907,788 | B1 | 3/2018 | Osborne |
| 10,105,354 | B1 | 10/2018 | Osborne |
| 10,172,841 | B2 | 1/2019 | Osborne |
| 10,940,142 | B2 | 3/2021 | Osborne |
| 11,129,818 | B2 | 9/2021 | Osborne et al. |
| 11,793,796 | B2 | 10/2023 | Osborne |
| 11,819,496 | B2 | 11/2023 | Osborne |
| 2005/0112162 | A1 | 5/2005 | Drader |
| 2005/0244339 | A1 | 11/2005 | Jauernig et al. |
| 2006/0084684 | A1 | 4/2006 | Bolle |
| 2006/0110415 | A1 | 5/2006 | Gupta |
| 2006/0153905 | A1 | 7/2006 | Carrara et al. |
| 2006/0204452 | A1 | 9/2006 | Lathrop et al. |
| 2006/0204526 | A1 | 9/2006 | Lathrop |
| 2006/0234006 | A1 | 10/2006 | Terra |
| 2007/0048241 | A1 | 3/2007 | Obukowho et al. |
| 2007/0098660 | A1 | 5/2007 | Taneri et al. |
| 2007/0207107 | A1 | 9/2007 | Winckle et al. |
| 2007/0258935 | A1 | 11/2007 | McEntire et al. |
| 2007/0259009 | A1 | 11/2007 | Inder |
| 2007/0287689 | A1 | 12/2007 | Harada |
| 2008/0020005 | A1 | 1/2008 | Chang et al. |
| 2008/0045572 | A1 | 2/2008 | Linder |
| 2008/0280958 | A1 | 11/2008 | Bolle et al. |
| 2009/0104132 | A1 | 4/2009 | Segura-Orsoni |
| 2009/0214628 | A1 | 8/2009 | De Rijk |
| 2009/0220583 | A1 | 9/2009 | Pereswetoff-Morath et al. |
| 2011/0117182 | A1 | 5/2011 | Ahluwalia et al. |
| 2011/0212157 | A1 | 9/2011 | Edelson et al. |
| 2012/0252793 | A1 | 10/2012 | Bream et al. |
| 2013/0005816 | A1 | 1/2013 | Chen |
| 2013/0017282 | A1 | 1/2013 | Ma |
| 2013/0018104 | A1 | 1/2013 | Lathrop et al. |
| 2013/0217742 | A1 | 8/2013 | Yang |
| 2014/0112991 | A1 | 4/2014 | Johnson et al. |
| 2014/0275265 | A1 | 9/2014 | Mattison |
| 2014/0296191 | A1 | 10/2014 | Patel et al. |
| 2014/0303215 | A1 | 10/2014 | Bolle et al. |
| 2015/0099752 | A9 | 4/2015 | Bernal Anchuela et al. |
| 2015/0297601 | A1 | 10/2015 | Henkin |
| 2016/0030435 | A1 | 2/2016 | Henkin |
| 2017/0152273 | A1 | 6/2017 | Merchant |
| 2017/0266289 | A1 | 9/2017 | Kipari |
| 2018/0353490 | A1 | 12/2018 | Osborne |
| 2019/0091333 | A1 | 3/2019 | Osborne |
| 2019/0175491 | A1 | 6/2019 | Abraham et al. |
| 2019/0365642 | A1 | 12/2019 | Osborne |
| 2020/0155524 | A1 | 5/2020 | Welgus et al. |
| 2020/0163944 | A1 | 5/2020 | Osborne et al. |
| 2021/0161870 | A1 | 6/2021 | Welgus et al. |

FOREIGN PATENT DOCUMENTS

| | | | |
|---|---|---|---|
| CN | 101541321 | A | 9/2009 |
| CN | 101854907 | | 10/2010 |
| CN | 108992673 | A | 12/2018 |
| CN | 112384199 | | 2/2021 |
| EP | 1511516 | A1 | 3/2005 |
| JP | 2005529930 | A | 10/2005 |
| JP | 2007119432 | A | 5/2007 |
| JP | 2007533606 | A | 11/2007 |
| JP | 2011219364 | A | 11/2011 |
| JP | 2012532871 | A | 12/2012 |
| WO | 9501338 | A1 | 1/1995 |
| WO | 9810768 | A1 | 3/1998 |
| WO | 2003/099334 | A1 † | 12/2003 |
| WO | WO 2003/099334 | A1 | 12/2003 |
| WO | WO 2005/016296 | A1 | 2/2005 |
| WO | 2009034537 | A2 | 3/2009 |
| WO | 2013030789 | A1 | 3/2013 |
| WO | 2013081565 | A1 | 6/2013 |
| WO | 2014055801 | A1 | 4/2014 |
| WO | 2014178065 | A1 | 6/2014 |
| WO | 2014130922 | | 8/2014 |
| WO | 2015132708 | A1 | 9/2015 |
| WO | 2016/033308 | A1 † | 3/2016 |
| WO | 2017216738 | | 12/2017 |
| WO | 2018144093 | A2 | 8/2018 |
| WO | 2018226584 | | 12/2018 |
| WO | 2019/060379 | A1 | 3/2019 |
| WO | 2021045804 | | 3/2021 |

OTHER PUBLICATIONS

Office Action issued in MX/a/2019/014741 dated Nov. 4, 2022 (7 pages).
Bardin P et al. Roflumilast for asthma: Efficacy findings in mechanism of action studies:. Pulmonary Pharmacology & THERAPEUTICS, vol. 35, Aug. 19, 2015, S4-S10.
Brown, "Treating COPD with PDE 4 inhibitors", International Journal of COPD 2007: 2(4) 517-533.
Examination Report cited in India Application No. 20194705011 dated Jul. 9, 2021. 7 pages.
Examination Report cited in India Application No. 202047016247 dated Jun. 28, 2021. 4 pages.
International Preliminary Report on Patentability and Written Opinion cited PCT/US2018/051691 dated Mar. 24, 2020. 6 pages.
International Search Report issued in PCT/US2021/031144 dated Sep. 21, 2021. 2 pages.
Julian N. Mayba et al. Review of Atopic Dermatitis and Topical Therapies:, Journal of Cutaneous Medicine and Surgery, BC Decker Inc. CA. vol. 21 No. 3 Dec. 27, 2016, pp. 227-236.
Kawamatawong, Roles of roflumilast, a selective phosphodiesterase 4 inhibitor in airway diseases:, J. Thorac Dis 2017. 9(4). 1144-1154.
Kircik, L et al., Rational Vehicle Design Ensures Targeted Cutaneous Steroid Delivery. Journal of Clinical and Aesthetic Dermatology 10(2). Feb. 2017. pp. 12-19.
Notification of Transmittal of the International Search Report and The Written Opinion of the International Searching Authority cited in PCT/US2020/29008 dated Jul. 6, 2020. 6 pages.
Notification of Transmittal of the International Search Report and Written Opinion cited in PCT/US2019/034640 dated Dec. 4, 2019, 10 pages.
Notification of Transmittal of the International Search Report and the Written Opinion of the International Searching Authority cited in PCT/US2021/015740 dated Apr. 23, 2021. 17 pages.
Notification of Transmittal of the International Search Report and Written Oinion of the International Searching Authority issued in PCT/US2022/013344 dated Jun. 9, 2022, 16 pages.
PCT International Search Report and Written Opinion issued in PCT/US2018/0358584 dated Aug. 17, 2018, 5 pages.
Special Chem "Ethoxydiglycol ," printed 2019; https://cosmetics.specialchem.com/inci/ethoxydiglycol, 4 pgs.
Translation Abstract. of Office Action for Chinese Patent Application No. 201810581282.7 dated Oct. 22, 2019; 13 pages.
Wikipedia "Corticosteroid," last edited Nov. 15, 2019; https://en.wikipedia.org/wiki/Corticosteroid, 14 pgs.
Wittmann et al. "Phosphodiesterase 4 Inhibition in the Treatment of Psoriasis, Psoratic Arthritis and Other Chronic Inflammatory Diseases". Dermatol Ther(Heidelb) (2013) 3:1-15.
Akhtar et al., "Exploring preclinical and clinical effectivenss of nanoformulations in the treatment of atopic dermatitis: Safety aspects and patent reviews", Bulletin of Faculty of Pharmacy, Cairo University 55 (2017), 1-10.
Karande et al., "Enhancement of transdermal drug delivery via synergistic action of chemicals", Biochimica Et Biophysica Acta, 1788 (2009), pp. 2632-2373.
Lorimer, "Thermodynamics of solubility in mixed solvent systems", Pure & Appl. Chem., 1993, vol. 65, 2, pp. 183-191.
Minghetti et al., "Ex Vivo Study of Transdermal Permeation of Four Diclofenac Salts from Different Vehicles", Journal of Pharmaceutical Sciences, vo. 96, No. 4, Apr. 2007, pp. 814-823.
Nair et al., "Basic considerations in the dennatokinetics of topical formulations", Brazilian Journal of Pharmaceutical Sciences, vol. 43, No. 3, Jul./Sep. 2013, pp. 423-434.

(56) References Cited

OTHER PUBLICATIONS

Osborne, "Diethylene glycol monoethyl ether: an emerging solvent in topical dermatology products", J. Cosmet Dermatol, Dec. 2011, 10(4), pp. 324-329, Abstract.
Pathan et al., "Chemical Penetration Enhancers for Transdermal Drug Delivery Systsms", Tropical Journal of Pharmaceutical Research, Apr. 2009, 8(2), pp. 173-179.
Sikarra et al., "Techniques for Solubility Enhancement of Poorly Soluble Drugs: An Overview", Journal of Medical Pharmaceutical and Allied Sciences. (2012). 01; pp. 1-22.
Tradename (roflumilast) Tablets NDA 22-522, Summary of Basis for the Recommended Action from Chemistry, Manufacturing, and Controls, Forest Research Institute, Inc., Reference ID 2901509, 3 pages, Date: Feb. 4, 2010.
Snape et al., "A phase I randomized trial to assess the effect on skin infiltrate thickness and tolerability of topical phosphodiesterase inhibitors in the treatment of psoriasis vulgaris using a modified psoriasis plaque test", British Journal of Dermatology (2016) 175, pp. 479-486.
Pudipeddi et al., "Trends in Solubility of Polymorphs", Journal of Pharmaceutical Sciences, May 2005, vol. 94, Issue 5, pp. 929-939, Abstract only.
Patzelt et al., "Hair follicles, their disorders and their opportunities", Drug Discovery Today: Disease Mechanisms, vol. 5, Issue 2, Summer 2008, pp. e173-e-181.
International Search Report and Written Opinion cited in PCT/US2018/051691 dated Nov. 22, 2018, 11 pages.
Shakeel et al., "Solubilization behavior of paracetamol in Transcutol-water mixtures at (298.15 to 333.15) K", Journal of Chemical & Engineering Data 58: 3551-3556, 2013.
Sullivan DW Jr, Gad SC, Julien M. A review of the nonclinical safety of Transcutol(R), a highly purified form of diethylene glycol monoethyl ether (DEGEE) used as a pharmaceutical excipient. Food Chem Toxicol. 2014;72:40-50.
Helton DR, Osborne DW, Pierson SK, Buonarati MH, Bethem RA. Pharmacokinetic profiles in rats after intravenous, oral, or dermal administration of dapsone. Drug Metab Dispos. 2000;28(8):925-9.
Gad SC, Cassidy CD, Aubert N, Spainhour B, Robbe H. Nonclinical vehicle use in studies by multiple routes in multiple species. Int J Toxicol. 2006;25(6):499-521.
Chadha G, Sathigari S, Parsons DL, Jayachandra Babu R. In vitro percutaneous absorption of genistein from topical gels through human skin. Drug Dev Ind Pharm. 2011;37(5):498-505.
Ganem-Quintanar A, Lafforgue C, Falson-Rieg F, Buri P. Evaluation of the transepidermal permeation of diethylene glycol monoethyl ether and skin water loss. Int J Pharm. 1997;147(2):165-71.
Dugard PH, Walker M, Mawdsley SJ, Scott RC. Absorption of some glycol ethers through human skin in vitro. Environ Health Perspect. 1984;57:193-7.
Koprda V, Bohacik L, & Hadgraft J Permeation of a Pyridoindol structure substance from the Transcutol/water/azone cosolvent system. In 5th International conference: Perspectives in Percutaneous Penetration. vol. 5B, pp. 163-164; 1997.
Ritschel WA, Hussain AS. In vitro skin penetration of griseofulvin in rat and human skin from an ointment dosage form. Arzneimittelforschung. 1988;38(11):1630-2.
Bialik W, Walkers KA, Brain KR, Hadgraft J. Some factors affecting the in vitro penetration of ibuprofen through human skin. Int J Pharm. 1993;92:219-23.
Yazdanian M, Chen E. The effect of diethylene glycol monoethyl ether as a vehicle for topical delivery of ivermectin. Vet Res Commun. 1995;19(4):309-19.
Bjorklund S, et al. The effects of polar excipients transcutol and dexpanthenol on molecular mobility, permeability, and electrical impedance of the skin barrier. J Colloid Interface Sci. 2016;479:207-20.
Benson HA. Transdermal drug delivery: penetration enhancement techniques. Curr Drug Deliv. 2005;2(1):23-33.
Gwak HS, Kim SU, Chun IK. Effect of vehicles and enhancers on thein vitro permeation of melatonin through hairless mouse skin. Arch Pharm Res. 2002;25(3):392-6.
Harrison JE, Watkinson AC, Green DM, Hadgraft J, Brain K. The relative effect of azone and Transcutol on permeant diffusivity and solubility in human stratum corneum. Pharm Res. 1996;13(4):542-6.
Otto A, Wiechers JW, Kelly CL, Hadgraft J, du Plessis J. Effect of penetration modifiers on the dermal and transdermal delivery of drugs and cosmetic active ingredients. Skin Pharmacol Physiol. 2008;21(6):326-34.
Bonina FP, Montenegro L. Effects of some non-toxic penetration enhancers on in vitro heparin skin permeation from gel vehicles. Int J Pharm. 1994;111(2):191-6.
Puglia C, Bonina F, Trapani G, Franco M, Ricci M. Evaluation of in vitro percutaneous absorption of lorazepam and clonazepam from hydro-alcoholic gel formulations. Int J Pharm.2001;228(1-2):79-87.
Godwin DA, Kim NH, Felton LA. Influence of Transcutol CG on the skin accumulation and transdermal permeation of ultraviolet absorbers. Eur J Pharm Biopharm. 2002;53(1):23-7.
Ritschel WA, Panchagnula R, Stemmer K, Ashraf M. Development of an intracutaneous depot for drugs. Binding, drug accumulation and retention studies, and mechanism of depot. Skin Pharmacol. 1991;4(4):235-45.
Remane Y, Leopold CS, Maibach HI. Percutaneous penetration of methyl nicotinate from ointments using the laser Doppler technique: bioequivalence and enhancer effects. J Pharmacokinet Pharmacodyn. 2006;33(6):719-35.
Panchagnula R, Ritschel WA. Development and evaluation of an intracutaneous depot formulation of corticosteroids using Transcutol as a cosolvent: in-vitro, ex-vivo and in-vivo rat studies. J Pharm Pharmacol. 1991;43(9):609-14.
Cho YA, Gwak HS. Transdermal delivery of ketorolac tromethamine: effects of vehicles and penetration enhancers. Drug Dev Ind Pharm. 2004;30(6):557-64.
Salimi A, Hedayatipour N, Moghimipour E. The effect of various vehicles on the naproxen permeability through rat skin: a mechanistic study by DSC and FT-IR techniques. Adv Pharm Bull. 2016;6(1):9-16.
Moghadam SH, Saliaj E, Wettig SD, Dong C, Ivanova MV, Huzil JT, et al. Effect of chemical permeation enhancers on stratum corneum barrier lipid organizational structure and interferon alpha permeability. Mol Pharm. 2013;10(6):2248-60.
Watkinson AC, Hadgraft J, Bye A. Aspects of the transdermal delivery of prostaglandins. Int J Pharm. 1991;74(2-3):229-36.
Gwak H, Chun I. Effect of vehicles and penetration enhancers on the in vitro percutaneous absorption of tenoxicam through hairless mouse skin. Int J Pharm. 2002;236(1-2):57-64.
Gwak HS, Oh IS, Chun IK. Transdermal delivery of ondansetron hydrochloride: effects of vehicles and penetration enhancers. Drug Dev Ind Pharm. 2004;30(2):187-94.
Chang RK, Raw A, Lionberger R, Yu L. Generic development of topical dermatologic products: formulation development, process development, and testing of topical dermatologic products. AAPS J. 2013;15(1):41-52.
Choi JS, Cho YA, Chun IK, Jung SY, Gwak HS. Formulation and evaluation of ketorolac transdermal systems. Drug Deliv. 2007;14(2):69-74.
Hirata K, Helal F, Hadgraft J, Lane ME. Formulation of carbenoxolone for delivery to the skin. Int J Pharm. 2013;448(2):360-5.
Hirata K, Mohammed D, Hadgraft J, Lane ME. Influence of lidocaine hydrochloride and penetration enhancers on the barrier function of human skin. Int J Pharm. 2014;477(1-2):416-20.
Mura P, Faucci MT, Bramanti G, Corti P. Evaluation of transcutol as a clonazepam transdermal permeation enhancer from hydrophilic gel formulations. Eur J Pharm Sci. 2000;9(4):365-72.
Kim KH, Gwak HS. Effects of vehicles on the percutaneous absorption of donepezil hydrochloride across the excised hairless mouse skin. Drug Dev Ind Pharm. 2011;37(9):1125-30.
Rhee YS, Huh JY, Park CW, Nam TY, Yoon KR, Chi SC, et al. Effects of vehicles and enhancers on transdermal delivery of clebopride. Arch Pharm Res. 2007;30(9):1155-61.

(56) References Cited

OTHER PUBLICATIONS

Touitou E, Levi-Schaffer F, Shaco-Ezra N, Ben-Yossef R, Fabin B. Enhanced permeation of theophylline through the skin and its effect on fibroblast proliferation. Int J Pharm. 1991;70(1-2):159-66.

Touitou E, Levi-Schaffer F, Dayan N, Alhaique F, Riccieri F. Modulation of caffeine skin delivery by carrier design: liposomes versus permeation enhancers. Int J Pharm. 1994;103(2):131-6.

Fabin B, Touitou E. Localization of lipophilic molecules penetrating rat skin in vivo by quantitative autoradiography. Int J Pharm. 1991;74(1):59-65.

Ayala-Bravo HA, Quintanar-Guerrero D, Naik A, Kalia YN, Cornejo-Bravo JM, Ganem-Quintanar A. Effects of sucrose oleate and sucrose laureate on in vivo human stratum corneum permeability. Pharm Res. 2003;20(8):1267-73.

Csizmazia E, Erős G, Berkesi O, Berkó S, Szabó-Révész P, Csányi E. Penetration enhancer effect of sucrose laurate and Transcutol on ibuprofen. J Drug Deliv Sci Technol. 2011;21(5):411-415.

Cazares-Delgadillo J, Naik A, Kalia YN, Quintanar-Guerrero D, Ganem-Quintanar A. Skin permeation enhancement by sucrose esters: a pH-dependent phenomenon. Int J Pharm. 2005;297(1-2):204-212.

Gungor S, Bergisadi N. Effect of penetration enhancers on in vitro percutaneous penetration of nimesulide through rat skin. Pharmazie. 2004;59(1):39-41.

Barakat NS. Evaluation of glycofurol-based gel as a new vehicle for topical application of naproxen. AAPS PharmSciTech. 2010;11(3):1138-46.

Javadzadeh Y, Hamishehkar H. Enhancing percutaneous delivery of methotrexate using different types of surfactants. Colloids Surf B Biointerfaces. 2011;82(2):422-6.

Senyigit T, Padula C, Ozer O, Santi P. Different approaches for improving skin accumulation of topical corticosteroids. Int J Pharm. 2009;380(1-2):155-60.

Berkó S, et al.Monitoring of skin penetration and absorption with a new in vivo experimental model. Farmacia. 2014;62(6):1157-63.

Tiossi RF, et al. In vitro and in vivo evaluation of the delivery of topical formulations containing glycoalkaloids of Solanum lycocarpum fruits. Eur J Pharm Biopharm. 2014;88(1):28-33.

Ritschel WA, Barkhaus JK. Use of sorption promoters to increase systemic absorption of coumarin from transdermal drug delivery systems. Arzneimittelforschung. 1988;38(12):1774-7.

Ritschel WA, Barkhaus JK. Feasibility study for transdermal delivery of meperidine. Methods Find Exp Clin Pharmacol. 1988;10(7):461-466.

Shaaya AN, Kraus C, Bauman DH, Ritschel WA. Pharmacokinetics and bioavailability of papaverine HCl after intravenous, intracorporeal and penis topical administration in beagle dogs. Methods Find Exp Clin Pharmacol. 1992;14(5):373-8.

Rougier A, Dupuis D, Lotte C Roguet R, , & H. Schaefer (1983) In vivo correlation between stratum corneum reservoir function and percutaneous absorption. J Invest Dermatol 81(275-278):275, 278; 1983.

Sutton et al., "Characterization of a Liquid Crystal Stabilized Pharmaceutical Oil-in-Water Emulsion Optimized for Skin Delivery", Journal of Cosmetics, Dermatological Sciences and Applications, vol. 8, No. 4, Nov. 2018, pp. 207-217.

V. Koprda et al., Skin Penetration Studies of Transcutol Using Radiotracer Technique, GRC (1995), 10 pgs.

Osborne et al., "Skin Penetration and Permeation Properties of Transcutol®-Neat or Diluted Mixtures", AAPS PharmaSCITECH, vol. 19, No. 8, Nov. 2018, pp. 3512-3533.

Notification of Reasons for Rejection issued in JP2020-567451 dated Nov. 24, 2023, 9 pgs.

T. Gao, et al., "Sunscreen Formulas with Multilayer Lamella Structure," Cosmetics & Toiletries, vol. 118, pp. 41-52 (Oct. 2003).

D.Y.M. Leung, et al., "New Insights into Atopic Dermatitis," J. Clin. Invest., vol. 113, pp. 651-657 (2004).

L. Kircik, "Topical Treatment Adherence for Psoriasis," Skin Therapy Letter-Family Practice Edition, vol. 4, No. 2, pp. 4 & 5 (2008).

S.R. Feldman, et al., "Psoriasis: Improving Adherence to Topical Therapy," J. Am. Acad. Dermatol., vol. 59, pp. 1009-1016 (2008).

S.M. Ali, et al., "Skin pH: From Basic Science to Basic Skin Care," Acta Derm. Venereal., vol. 93, pp. 261-67 (1-9), Tbl. SI (2013).

Study NCT01856764, "Topical Roflumilast in Adults with Atopic Dermitis" sponsored by Takeda, available at https://clinicaltrials.gov/ (Jul. 2015).

Y. Javadzadeh, et al., "Transcutol® (Diethylene Glycol Monoethyl Ether): A Potential Penetration Enhancer," Ch. 12, pp. 195-205, in N. Dragicevic, et al., eds., Percutaneous Penetration Enancers Chemical Methods in Penetration Enhancemeent: Modification of the Stratum Corneum (2015).

FDA, Inactive Ingredient Guide (Jan. 1996).

M.J. O'Neil, et al., eds., The Merck Index, pp. 2822, 8379 (15th ed., 2013).

Labeling for Elocon® (mometasone furoate) Cream (2013).

Labeling for Daliresp® (roflumilast) Tablets (2013).

Physician's Desk Reference, pp. 305, 748-752, 1432-1435 (67th/ 2013 ed., 2012).

I.M. Rosenstock, "Understanding and Enhancing Patient Compliance with Diabetic Regimens," Diabetes Care, vol. 8, pp. 610-616 (1985).

J. Urquhart, "The Electronic Medication Event Monitor: Lessons for Pharmacotherapy," Clin. Pharmacokinet., vol. 32, pp. 345-356 (1997).

S.S. Zaghloul, et al., "Objective Assessment of Compliance with Psoriasis Treatment," Arch. Dermatol., vol. 140, pp. 408-414 (2004).

P. Assawasuwannakit, et al., "Quantification of the Forgiveness of Drugs to Imperfect Adherence," CPT Pharmacometrics Syst. Pharmacol., vol. 4, e4, pp. 1-8 (2015).

Office Action issued in U.S. Appl. No. 18/453,674 dated Oct. 27, 2023 (13 pages).

Office Action issued in U.S. Appl. No. 17/155,679 dated Feb. 5, 2024 (9 pages).

Office Action issued in U.S. Appl. No. 18/345,692 dated Oct. 26, 2023 (68 pages).

Office Action issued in U.S. Appl. No. 18/345,732 dated Jan. 24, 2024 (12 pages).

Notification of Certification of Invalidity, Unenforceability, and/or Noninfringement for U.S. Pat. Nos. 9,884,050; 9,907,788; 10,940,142; 11,129,818; 11,793,796; and 11,819,496 Pursuant to § 505(j)(2)(B)(iv) of the Federal Food, Drug, & Cosmetic Act, Feb. 13, 2024, 198 pages.

† cited by third party

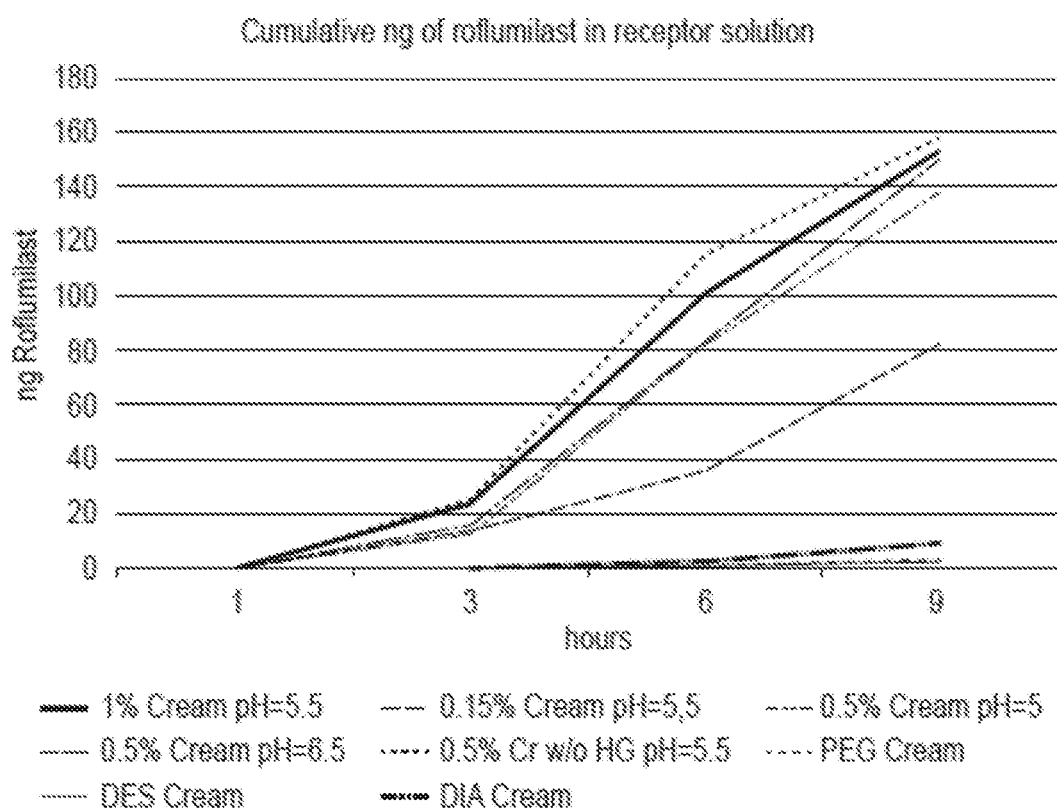

METHOD AND FORMULATION FOR IMPROVING ROFLUMILAST SKIN PENETRATION LAG TIME

CROSS REFERENCE TO RELATED APPLICATIONS

This application claims the benefit of U.S. Provisional Application No. 62/680,203 filed Jun. 4, 2018 and U.S. Provisional Application No. 62/742,644 filed on Oct. 8, 2018, the disclosures of which are incorporated herein in their entirety by reference.

BACKGROUND OF INVENTION

Pharmacokinetics is the study of the movement of a drug within a patient's body over time. There are four phases used to determine the pharmacokinetics of a drug, absorption, distribution, metabolism and excretion. Absorption after topical application is the process of drug movement from the application site across one or more cell membrane barriers into the circulation. The absorption of topically administered drugs is important for dermatological treatments and for topical application of systemic medications. After topical administration, the drugs must first be absorbed into the skin. Drug metabolism can occur in the skin or the drug may reach the systemic circulation before it is metabolized. After a topically administered drug reaches the systemic circulation, its fate is similar to that of systemically administered drugs. The concentrations of a drug that reach the target site after topical administration is highly dependent on the characteristics of both the drug itself and its formulation, as well as the characteristics of the patient's skin.

The healthy skin of a pig or human will absorb a pharmaceutical active from a topically applied semisolid in a very predictable way. Following the onset of skin exposure to a compound, the cumulative influx into the skin follows the time course shown in FIG. 1(a), whereas the outflux of the same compound into the vasculature displays a time course shown in FIG. 1(b). The influx rate starts at a higher rate because there is initially no compound in the skin, or more precisely no drug is in the intercellular spaces of the stratum corneum. The higher influx rate is due to the concentration of drug in a non-volatile product being at its highest concentration upon initial dosing of the topical semisolid which results in the thermodynamic driving force of drug influx into the skin being at its maximum. At this point, the outflux into the vasculature is negligible.

Robinson defines "lag time" this way (P. J. Robinson, "Prediction—Simple Risk Models and Overview of Dermal Risk Assessment" Chapter 8, pages 203-229 in Dermal Absorption and toxicity Assessment edited by Michael S. Roberts and Kenneth A. Walters. Marcel Dekker, New York 1998 page 215): "After a while, drug builds up in the skin and outflux into the blood increases. Eventually, sufficient material builds up in the skin itself that a steady state is reached in which influx into the skin equals outflux from the skin into the vasculature. After such a 'lag time', which depends on the compound and may be an hour or more, the curves (a) and (b) have the same slope (given essentially by the dermal penetration coefficient $K_p$)." It should be noted that the total amount of drug that has entered the skin (influx) is always greater than the amount of drug that has entered the vasculature (outflux). In other words, curve (a) in FIG. 1 is always above curve (b).

Mathematically, the dermal penetration coefficient Kp can be solved using Fick's Laws of Diffusion derived by Adolf Fick in 1855.

Figure 2:
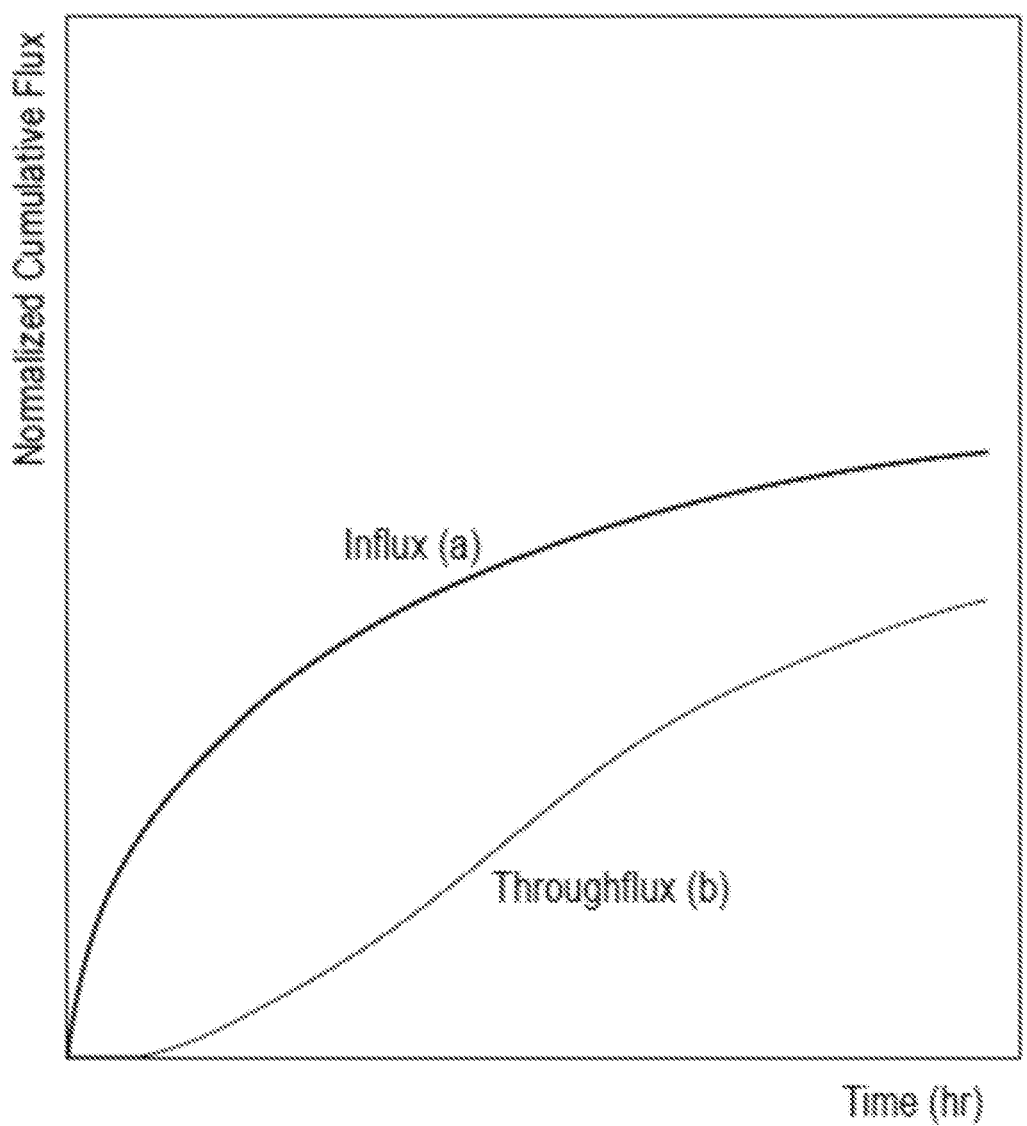

For clinically relevant dosing in which a finite amount of topical semisolid is rubbed into diseased skin, the cumulative influx of active into the skin (FIG. 2a) and outflux into the vasculature (FIG. 2b) will have a significantly different time course. Since the duration of exposure to a compound is limited, a plateau occurs in the time course curve for influx into the skin, which is mirrored by a plateau in the outflux into the vasculature curve. For a single dose application, eventually the two plateau lines will become parallel with the difference in magnitude representing the percent of applied dose absorbed. As a practical matter, when a patient is being treated topically for a skin disease, a second dose is applied prior to the cumulative skin influx curve and cumulative vasculature outflux curve becoming truly parallel. However, two aspects of how a topically applied pharmaceutical active penetrates skin rigorously holds; 1) a lag time exists between influx into the skin and outflux into the vasculature and 2) the amount of drug entering the skin is always greater than the amount of drug entering the vasculature. These two rules apply to dosing humans or mammals either ex vivo, in vitro, or in vivo using clinically relevant finite dosing or infinite dosing used in in vitro membrane diffusion experiments.

To better understand the first aspect of topical skin penetration stated above, it should be noted that the lag time between influx into the skin and outflux into the vasculature measured using in vitro penetration testing (IVPT) can be dramatically shorter compared to the lag time for the active to achieve measurable blood concentrations in a pharmacokinetic (PK) study. For IVPT, excised human skin is cut to a depth of 200-600 micrometers which assures an intact stratum corneum and skin barrier, but cuts away the lower dermis that resides below the network of skin vasculature that removes actives from the skin, i.e. vascular outflux. The skin is cut using a dermatome and mounted on a diffusion cell that allows dosing of a formulation onto the stratum corneum and sampling of a receptor solution in contact with the cut surface of the dermis. The time point that measurable concentrations of active appears in the receptor solution can be extrapolated to calculate the lag time with the assumption that the time course of passive diffusion through the stratum corneum, epidermis and upper dermis is similar for excised skin and intact skin of a subject being dosed topically. For a PK study, once active has entered the vasculature and skin outflux has begun, multiple mechanisms dilute or remove the active from the blood to concentrations below the bioanalytical method detection limit. Since PK sampling is completed remotely from the site of topical product application (dose the back, but pull blood from the arm), the initial outflux is diluted by the blood volume of the subject (mammal or human) being studied. The drug outfluxed from the skin into the vasculature will then undergo distribution into the tissues, metabolism and excretion characteristic of the drug further delaying detection in the blood and extending lag time. These PK parameters, such as volume of distribution and drug half-life are characterized using intravenous dosing of the drug and contrasted to results after topical application to determine dermal bioavailability of the topically applied dermatological formulation (M. S. Roberts and K. A. Walters, "The Relationship Between Structure and Barrier Function of Skin" Chapter 1, pages 1-42 in Dermal Absorption and toxicity Assessment edited by Michael S. Roberts and Kenneth A. Walters. Marcel Dekker, New York 1998 page 21). Thus, the lag time measured using IVPT is shorter than the lag time measured in PK experiments, because achieving measurable blood levels of active always takes longer than for active to diffuse to the depth in the skin required to reach the vasculature for outflux from the skin.

As stated above in the quote from Robinson, it is well established that lag time depends on the compound penetrating the skin and may be an hour or more. It is also well established that skin penetration enhancers (Osborne & Henke reference), excipients combined with the pharmaceutical active to formulate a topical product, can influence lag time as well as increase the amount of active crossing the stratum corneum. For this reason, scientists that develop topical pharmaceutical products often use IVPT to screen multiple prototype formulations to select which final composition to advance into the non-clinical and clinical studies required to advance a dermatological product through the approval process. During development of topical roflumilast for the treatment of inflammatory skin conditions, it was discovered that roflumilast dissolved in a topically applied formulation containing an emulsifier, wherein the formulation has a pH value between 4.0-6.5 had a surprisingly short lag time of less than 1 hour when applied to a living mammal.

Roflumilast and its synthesis were described in U.S. Pat. No. 5,712,298 (the "'298 patent"), incorporated herein by reference (*unless otherwise indicated, all references incorporated herein by reference are incorporated in their entireties for all purposes). It has long been recognized that pharmaceutical compounds having phosphodiesterase (PDE)-inhibiting properties, such as roflumilast, are useful for treating psoriasis and atopic dermatitis ('298 patent, col 11 lines 52-61) and other chronic inflammatory and allergen-induced dermatoses. For treatment of such dermatoses, roflumilast emulsions, suspensions, gels or solutions for topical application have been described ('298 patent, col 12, lines 37-64).

Topical application of potent pharmacological agents like roflumilast for treating skin diseases has been found to provide superior delivery, lower systemic exposure and greater ease of use for patients. The molecular structure of the compound ultimately dictates the ability of the drug to cross the epithelium of the tissue to which the product is applied. For topical application to skin, selection of the components of the formulation dictates the maximum skin permeation that the formulator can achieve. Creams, lotions, gels, ointments and foams are just a few of the more familiar forms of topical products that contain active pharmaceutical ingredients (API) for application to the skin.

The ability of a dissolved active ingredient to permeate the barrier of the skin is determined by its molecular structure. A well-known relationship between molecular structure and skin penetration is that increasing molecular weight decreases the rate that an active crosses the skin (J D Bos, M M Meinardi, Exp Dermatol. 2000 June; 9(3):165-9).

Another well-understood relationship is that increasing the octanol-water partition coefficient of a hydrophilic active initially increases the rate that an active permeates the skin, but then decreases skin permeation once the active becomes too lipophilic to partition out of the stratum corneum and into the lower layers of the epidermis (D. W. Osborne and W. J. Lambert, Prodrugs for Dermal Delivery, K. B. Sloane ed., Marcel Dekker, New York 163-178 (1992)). The optimal octanol-water partition coefficient is usually at log P values of 2-3. The rate that an active ingredient crosses into the viable epidermis can be further modified based on the composition of the topical product. Final pH of the formulation may be critical, because dissolved ionized active ingredients typically do not permeate the skin as effectively as active ingredients that do not carry a charge (N. Li, X. Wu, W. Jia, M. C. Zhang, F. Tan, and J Zhang. Drug Dev Indust Pharm 38(8)985-994). Functional ingredients such as skin penetration enhancers (D. W. Osborne and J. J. Henke, Pharmaceutical Technology 21(11)58-66(1997)) can be added to the topical product to increase skin permeation. For a dissolved active in the topical product, the closer the drug concentration is to the amount of active required to saturate the drug product, the greater the thermodynamic driving force of the active to cross the skin, i.e. the greater the skin flux of the active. The scientific literature guides formulators on how to increase penetration through the polar route, the nonpolar route, and the intercellular lipid pathway or trans-follicular penetration.

A method for decreasing skin penetration lag times will improve the bioavailability of topically administered roflumilast thereby improving the treatment outcome of topically treated skin conditions.

BRIEF DESCRIPTION OF THE DRAWINGS

FIG. 1 shows an idealized influx curve (a) compared to throughflux curve (b) after infinite dosing (Adapted from Robinson).

FIG. 2 shows an idealized influx curve (a) compared to throughflux curve (b) after finite dosing.

FIG. 3 shows that the five creams containing Crodafos CES as the emulsifier had measurable levels of roflumilast in the receptor solution one hour after dosing. These creams had essentially the same extrapolated lag times in the range of 50-60 minutes, slightly less than 1 hour when adjusted to pH values between 5.0 and 6.5.

SUMMARY OF THE INVENTION

In accordance with the present invention, it has been discovered that maintaining topically applied roflumilast at a pH value between 4.0-6.5 and/or combining roflumilast with specific emulsifiers results in skin penetration lag times of less than one hour. The surprisingly short lag time is particularly important in topically treating inflammatory skin conditions since it not only provides quicker onset of disease relief, but also allows for more consistent bioavailability of active since roflumilast spends less time on the skin surface, vulnerable to transference to clothing or other people.

DETAILED DESCRIPTION OF THE INVENTION

Roflumilast is a compound of the formula (I)

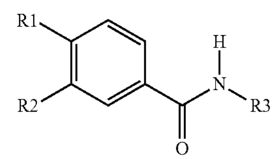

(I)

wherein R1 is difluoromethoxy, R2 is cyclopropylmethoxy and R3 is 3,5-dichloropyrid-4-yl.

This compound has the chemical name N-(3,5-dichloropyrid-4-yl)-3-cyclopropylmethoxy-4-difluoromethoxybenzamid-e (INN: roflumilast). Roflumilast can be prepared by methods known in the art (e.g. see the '298 patent and U.S. application Ser. No. 14/075,035).

Diethylene glycol monoethyl ether is a compound of the formula (II)

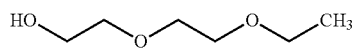

The emulsifier blend of cetearyl alcohol (CAS 67762 30 0), dicetyl phosphate (CAS 2197 63 9) and ceteth-10 phosphate (CAS 50643-20-4) which is manufactured by Croda under the tradename CRODAFOS™ CES. This commercially available emulsifier blend is a self-emulsifying wax that is predominately the waxy material cetearyl alcohol (which is a mixture cetyl alcohol ($C_{16}H_{34}O$) and stearyl alcohol ($C_{18}H_{38}O$)) combined with 10-20% dicetyl phosphate and 10-20% ceteth-10 phosphate. Self-emulsifying waxes form an emulsion when blended with water. When CRODAFOS™ CES is added to water it spontaneously forms an emulsion having a pH of about 3. Sodium hydroxide solution is added to increase the pH to the desired value.

wax blends of cetearyl alcohol, dicetyl phosphate and ceteth-10 phosphate (Croda Tradename CRODAFOS™ CES) and water with the pH value adjusted to between 4.0-6.5. This pH adjusted aqueous phosphate-ester based emulsifying wax optionally includes one or more pharmaceutically acceptable carriers. Any suitable grade of CRODAFOS™ can be used including CRODAFOS™ CES-PA and CRODAFOS™ CS20A. This blend of phosphate-ester self-emulsifying wax and water can undergo the addition of excipients and further processing to form a range of pharmaceutical dosage forms and maintain dissolved or molecularly dispersed roflumilast over the shelf life of the drug product.

The present invention is also directed to pharmaceutical compositions of roflumilast blended with DEGEE and the self-emulsifying wax blend of cetearyl alcohol, dicetyl phosphate and ceteth-10 phosphate and water with the pH value adjusted to 4.0-6.5.

The present invention is particularly useful for topical formulations. The topical roflumilast pharmaceutical product formulations that could be based on DEGEE-water blends are defined in U.S. Pharmacopeia USP <1151> and

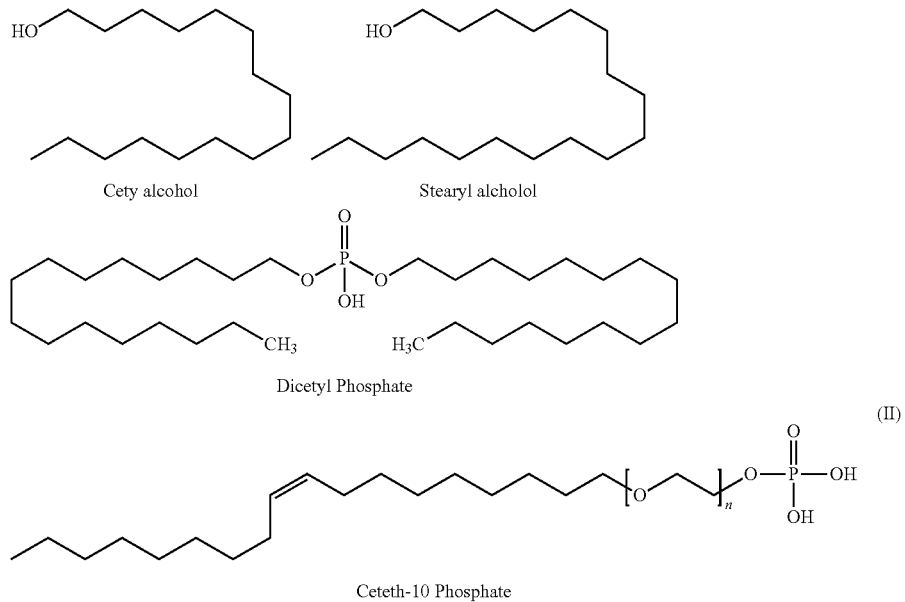

The present invention is directed to pharmaceutical compositions of roflumilast with the pH value adjusted to 4.0-6.5. In a preferred embodiment, roflumilast can be blended with diethylene glycol monoethyl ether (DEGEE, Gattefosse Tradename TRANSCUTOL®) and water. This pH adjusted aqueous DEGEE blend optionally includes one or more pharmaceutically acceptable carriers. Any suitable grade of TRANSCUTOL® can be used including TRANSCUTOL®P, TRANSCUTOL®HP, TRANSCUTOL®V and TRANSCUTOL®CG. This blend of DEGEE and water can undergo the addition of excipients and further processing to form a range of pharmaceutical dosage forms and maintain dissolved or molecularly dispersed roflumilast over the shelf life of the drug product. In another embodiment, hexylene glycol can be included in the roflumilast composition.

The present invention is also directed to pharmaceutical compositions of roflumilast blended with self-emulsifying include aerosols, foams, sprays, emulsions (which can also be called creams, lotions, or ointments), gels (two phase or single phase), liquids, ointments, pastes, shampoos, suspensions, and systems. These are typical dosage forms containing pharmaceutically active ingredients for topical application to mammals, including humans.

Topical application refers to dosing the skin, hair or nails of a patient that will benefit from treatment with a pharmaceutical product. Topical can also mean application to the epithelium of the patient for localized delivery. This includes but is not limited to ophthalmic, ottic, oral mucosa, vaginal mucosa, rectal mucosa or urethral application of roflumlast. The broadest definition of topical would include using the epithelium of a patient as a route of administration to obtain therapeutic systemic levels of the active ingredient. This definition of topical is often referred to as transdermal delivery of therapeutic active ingredients.

The roflumilast formulations can be prepared by methods known in the art (e.g. see the '298 patent and U.S. application Ser. No. 14/075,035).

DEGEE is often formulated as 10-30% (w/w), preferably 15-20% (w/w), in topical formulations. Likewise, water is formulated as about 20-90% (w/w) in topical products. For blends of DEGEE and water the ratio can range from 1:10 to 20:1. Preferably the DEGEE:water ratio is 1:4 to 9:1 in a formulation containing roflumilast.

Generally, DEGEE-water blends can be used to dissolve up to 2.0% roflumilast (in the finished product) or preferably up to 0.5% roflumilast (in the finished product). The finished product is preferably in one of the following forms:

An oil-in-water emulsion: The topical product may be an emulsion comprising a discrete hydrophobic phase and a continuous aqueous phase that includes the DEGEE-water blend and optionally one or more polar hydrophilic excipients as well as solvents, co-solvents, salts, surfactants, emulsifiers, and other components. These emulsions may include water-soluble or water-swellable polymers that help to stabilize the emulsion.

A water-in-oil emulsion: The compositions may be formulations in which roflumilast is incorporated into an emulsion that includes a continuous hydrophobic phase and an aqueous phase that includes the DEGEE-water blend and optionally one or more polar hydrophilic carrier(s) as well as salts or other components. These emulsions may include oil-soluble or oil-swellable polymers as well as one or more emulsifier(s) that help to stabilize the emulsion.

For both oil-in-water and water-in-oil emulsions, order of addition may be important. Roflumilast can be added pre-dissolved in the continuous aqueous phase containing the DEGEE-water blend. Likewise, roflumilast can be pre-dissolved in the hydrophobic discrete phase of the emulsion that is then mixed with the DEGEE-water blend and optional hydrophilic excipients that do not contain the active ingredient. Roflumilast can be pre-dissolved in both the oil phase and water phase of the emulsion or added pre-dissolved in DEGEE or a DEGEE-water blend after the emulsion has been formed. Some emulsions undergo phase inversion over a specific temperature range during cooling of the emulsion. Thus, roflumilast may be added to a water-in-oil emulsion above the phase inversion temperature, with the final drug product being an oil-in-water emulsion at controlled room temperature, or vice versa.

Thickened aqueous gels: These systems include the DEGEE-water blend with dissolved roflumilast and optionally one or more polar hydrophilic carrier(s) such as hexylene glycol which has been thickened by suitable natural, modified natural, or synthetic thickeners as described below. Alternatively, the thickened aqueous gels can be thickened using suitable polyethoxylate alky chain surfactants or other nonionic, cationic, or anionic systems.

Thickened hydroalcoholic gels: These systems include the DEGEE-water-alcohol blend with dissolved roflumilast and optionally one or more polar hydrophilic carrier(s) such as hexylene glycol as the polar phase which has been thickened by suitable natural, modified natural, or synthetic polymers such as described below. Alternatively, the thickened hydroalcoholic gels can be thickened using suitable polyethoxylate alky chain surfactants or other nonionic, cationic, or anionic systems. The alcohol can be ethanol, isopropyl alcohol or other pharmaceutically acceptable alcohol.

A hydrophilic or hydrophobic ointment: The compositions are formulated with a hydrophobic base (e.g. petrolatum, thickened or gelled water insoluble oils, and the like) and optionally have a minor amount of the DEGEE-water blend with dissolved roflumilast. Hydrophilic ointments generally contain one or more surfactants or wetting agents.

Solvents

Compositions of the present invention may include one or more solvents or co-solvents to obtain the desired level of active ingredient solubility in the product. The solvent may also modify skin permeation or activity of other excipients contained in a topical product. Solvents include but are not limited to acetone, ethanol, benzyl alcohol, butyl alcohol, diethyl sebacate, diethylene glycol monoethyl ether, diisopropyl adipate, dimethyl sulfoxide, ethyl acetate, isopropyl alcohol, isopropyl isostearate, isopropyl myristate, N-methyl pyrrolidinone, propylene glycol and SD alcohol.

Moisturizers

Compositions of the present invention may include a moisturizer to increase the level of hydration. For emulsions, the moisturizer is often a component of the discrete or continuous hydrophobic phase. The moisturizer can be a hydrophilic material including humectants or it can be a hydrophobic material including emollients. Suitable moisturizers include but are not limited to: 1,2,6-hexanetriol, 2-ethyl-1,6-hexanediol, butylene glycol, glycerin, polyethylene glycol 200-8000, butyl stearate, cetostearyl alcohol, cetyl alcohol, cetyl esters wax, cetyl palmitate, cocoa butter, coconut oil, cyclomethicone, dimethicone, docosanol, ethylhexyl hydroxystearate, fatty acids, glyceryl isostearate, glyceryl laurate, glyceryl monostearate, glyceryl oleate, glyceryl palmitate, glycol distearate, glycol stearate, isostearic acid, isostearyl alcohol, lanolin, mineral oil, limonene, medium-chain triglycerides, menthol, myristyl alcohol, octyldodecanol, oleic acid, oleyl alcohol, oleyl oleate, olive oil, paraffin, peanut oil, petrolatum, Plastibase-50W, and stearyl alcohol.

Surfactants and Emulsifiers

Compositions according to the present invention can optionally include one or more surfactants to emulsify the composition and to help wet the surface of the active ingredients or excipients. As used herein the term "surfactant" means an amphiphile (a molecule possessing both polar and nonpolar regions which are covalently bound) capable of reducing the surface tension of water and/or the interfacial tension between water and an immiscible liquid. Surfactants include but are not limited to alkyl aryl sodium sulfonate, Amerchol-CAB, ammonium lauryl sulfate, apricot kernel oil PEG-6 esters, Arlacel, benzalkonium chloride, Ceteareth-6, Ceteareth-12, Ceteareth-15, Ceteareth-30, cetearyl alcohol/ceteareth-20, cetearyl ethylhexanoate, ceteth-10, ceteth-10 phosphate, ceteth-2, ceteth-20, ceteth-23, choleth-24, cocamide ether sulfate, cocamine oxide, coco betaine, coco diethanolamide, coco monoethanolamide, coco-caprylate/caprate, dicetyl phosphate, disodium coco-amphodiacetate, disodium laureth sulfosuccinate, disodium lauryl sulfoacetate, disodium lauryl sulfosuccinate, disodium oleamido monoethanolamine sulfosuccinate, docusate sodium, laureth-2, laureth-23, laureth-4, lauric diethanolamide, lecithin, mehoxy PEG-16, methyl gluceth-10, methyl gluceth-20, methyl glucose sesquistearate, oleth-2, oleth-20, PEG 6-32 stearate, PEG-100 stearate, PEG-12 glyceryl laurate, PEG-120 methyl glucose dioleate, PEG-15 cocamine, PEG-150 distearate, PEG-2 stearate, PEG-20 methyl glucose sesqustearate, PEG-22 methyl ether, PEG-25 propylene glycol stearate, PEG-4 dilaurate, PEG-4 laurate, PEG-45/dodecyl glycol copolymer, PEG-5 oleate, PEG-50 Stearate, PEG-54 hydrogenated castor oil, PEG-6 isostearate, PEG-60 hydrogenated castor oil, PEG-7 methyl ether, PEG-75 lanolin, PEG-8 laurate, PEG-8 stearate, Pegoxol 7 stearate, pentaerythritol cocoate, poloxamer 124, poloxamer 181, poloxamer 182, poloxamer 188, poloxamer 237 poloxamer 407, polyglyceryl-3 oleate, polyoxyethylene alcohols, polyoxyethylene fatty acid esters, polyoxyl 20 cetostearyl ether, polyoxyl 40 hydrogenated castor oil, polyoxyl 40 stearate, polyoxyl 6 and polyoxyl 32, polyoxyl glyceryl stearate, polyoxyl stearate, polysorbate 20, polysorbate 40, polysorbate 60, polysorbate 65, polysorbate 80, PPG-26 oleate, PROMULGEN™ 12, propylene glycol diacetate, propylene glycol dicaprylate, propylene glycol monostearate, sodium xylene sulfonate, sorbitan monooleate, sorbitan monopalmitate, sorbitan monostearate, steareth-2, steareth-20, steareth-21, steareth-40, tallow glycerides, and emulsifying wax. The formulation preferably contains one or more phosphate ester surfactants. Examples of phosphate ester surfactants that may be included in the formulation include but are not limited to potassium cetyl phosphate, potassium C9-15 alkyl phosphate, potassium C11-15 alkyl phosphate, potassium C12-13 alkyl phosphate, potassium C12-14 alkyl phosphate, potassium lauryl phosphate, C8-10 alkyl ethyl phosphate, C9-15 alkyl phosphate, C20-22 alkyl phosphate, castor oil phosphate, ceteth-10 phosphate, ceteth-20 phosphate, ceteth-8 phosphate, cetearyl phosphate, cetyl phosphate, dimethicone PEG-7 phosphate, disodium lauryl phosphate, disodium oleyl phosphate, lauryl phosphate, myristyl phosphate, octyldecyl phosphate, oleth-10 phosphate, oleth-5 phosphate, oleth-3 phosphate, oleyl ethyl phosphate oleyl phosphate, PEG-26-PPG-30 phosphate, PPG-5ceteareth-10 phosphate, PPG-5 ceteth-10 phosphate, sodium lauryl phosphate, sodium laureth-4 phosphate, steartyl phosphate, DEA-cetyl phosphate, DEA-oleth-10 phosphate, DEA-oleth-3 phosphate, DEA-C8-C18 perfluoroalkylethyl phosphate, dicetyl phosphate, dilaureth-10 phosphate, dimyristyl phosphate, dioleyl phosphate, tricetyl phosphate, triceteareth-4 phosphate, trilaureth-4 phosphate, trilauryl phosphate, triolyeyl phosphate and tristearyl phosphate.

Polymers and Thickeners

For certain applications, it may be desirable to formulate a topical product that is thickened with soluble, swellable, or insoluble organic polymeric thickeners such as natural and synthetic polymers or inorganic thickeners including but not limited to acrylates copolymer, carbomer 1382, carbomer copolymer type B, carbomer homopolymer type A, carbomer homopolymer type B, carbomer homopolymer type C, caroboxy vinyl copolymer, carboxymethylcellulose, carboxypolymethylene, carrageenan, guar gum, hydroxyethyl cellulose, hydroxypropyl cellulose, microcrystalline wax, and methylcellulose.

Additional Components

Compositions according to the present invention may be formulated with additional components such as fillers, carriers and excipients conventionally found in cosmetic and pharmaceutical topical products. Additional components include but are not limited to antifoaming agents, propellants, preservatives, antioxidants, sequestering agents, stabilizers, buffers, pH adjusting solutions, skin penetration enhancers, film formers, dyes, pigments, fragrances and other excipients to improve the stability or aesthetics of the product. In a preferred embodiment, hexylene glycol is added to inhibit changes in particle size distribution over the shelf life of the composition. Hexylene glycol can be added between 0.1% and 20% on a weight/weight basis, preferably between 0.25% and 8% on a weight/weight basis and most preferably between 0.5% and 2% on a weight/weight basis.

In one preferred embodiment, the roflumilast is in the form of an aerosolized foam which is particularly suitable for application to the scalp. Any suitable propellant can be used to prepare the aerosolized foam. Particularly preferred propellants are Isobutane A-31, Aeropin 35, Butane 48, Dimethyl Ether/N-Butane-(53/47), Propane/Iso-Butane/N-Butane, Propane/Isobutane-A70, and Propane/Isobutane A-46, N-Butane (A-17.

Compositions according to the present invention may be formulated with additional active agents depending on the condition to be treated. The additional active agents include but are not limited to Anthralin (dithranol), Azathioprine, Tacrolimus, Coal tar, Methotrexate, Methoxsalen, Salicylic acid, Ammonium lactate, Urea, Hydroxyurea, 5-fluorouracil, Propylthouracil, 6-thioguanine, Sulfasalazine, Mycophenolate mofetil, Fumaric acid esters, Corticosteroids (e.g. Aclometasone, Amcinonide, Betamethasone, Clobetasol, Clocotolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), Acitretin, Tazarotene, Cyclosporine, Resorcinol, Colchicine, Adalimumab, Ustekinumab, Infliximab, bronchodialators (e.g. beta-agonists, anticholinergics, theophylline), and antibiotics (e.g. erythromycin, ciprofloxacin, metronidazole).

Administration and Dosage

Suitable pharmaceutical dosage forms include but are not limited to emulsions, suspensions, sprays, oils, ointments, fatty ointments, creams, pastes, gels, foams transdermal patches and solutions (e.g. injectable, oral).

The composition preferably contains roflumilast, salts of roflumilast, the N-oxide of roflumilast or salts thereof in an amount of 0.005-2% w/w, more preferably 0.05-1% w/w, and most preferably 0.1-0.5% w/w per dosage unit.

The composition preferably contains diethylene glycol monoethyl ether in an amount of between 5% and 50% w/w, more preferably between 20% and 30% w/w and most preferably between 22.5% and 27.5% w/w.

The composition can be administered one or more times per day, preferably the composition is administered 1-2 times per day.

The composition can be used in veterinary and in human medicine for the treatment and prevention of all diseases regarded as treatable or preventable by using roflumilast, including but not limited to acute and chronic airway disorders; proliferative, inflammatory and allergic dermatoses; disorders which are based on an excessive release of TNF and leukotrienes; disorders of the heart which can be treated by PDE inhibitors; inflammations in the gastrointestinal system or central nervous system; disorders of the eye; arthritic disorders; and disorders which can be treated by the tissue-relaxant action of PDE inhibitors. Preferably, the composition is used to treat proliferative, inflammatory and allergic dermatoses such as psoriasis (vulgaris), eczema, acne, Lichen simplex, sunburn, pruritus, alopecia areata, hypertrophic scars, discoid lupus erythematosus, and pyodermias.

The composition can include additional active agents suitable for treating the patient's condition. For example, when proliferative, inflammatory and allergic dermatoses are treated, the composition may additionally include Anthralin (dithranol), Azathioprine, Tacrolimus, Coal tar, Methotrexate, Methoxsalen, Salicylic acid, Ammonium lactate, Urea, Hydroxyurea, 5-fluorouracil, Propylthouracil, 6-thioguanine, Sulfasalazine, Mycophenolate mofetil, Fumaric acid esters, Corticosteroids (e.g. Aclometasone, Amcinonide, Betamethasone, Clobetasol, Clocotolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), Acitretin, Tazarotene, Cyclosporine, Resorcinol, Colchicine, Adalimumab, Ustekinumab, Infliximab, and/or antibiotics.

The following examples are provided to enable those of ordinary skill in the art to make and use the methods and compositions of the invention. These examples are not intended to limit the scope of what the inventors regard as their invention. Additional advantages and modifications will be readily apparent to those skilled in the art.

Example 1

TABLE 1

| 1.0% Roflumilast Cream Components | Composition % w/w |
|---|---|
| Roflumilast | 1.0, 0.5, 0.3, or 0.15 |
| Petrolatum, USP | 10.0 |
| Isopropyl Palmitate, NF | 5.0 |
| Crodafos CES cetostearyl alcohol dicetyl phosphate ceteth-10 phosphate | 10.0 |
| Diethylene Glycol Monoethyl Ether, NF (Transcutol P) | 25.0 |
| Hexylene Glycol, NF | 2.0 |
| Methylparaben, NF | 0.20 |
| Propylparaben, NF | 0.050 |
| 1N NaOH, NF | q.s. ad pH 5.5 |
| Purified Water, USP | q.s. ad 100% |

Male and female swine (Gottingen Minipig® breed) were ordered to weigh 8 to 12 kg at arrival. On the day prior to administration of topical cream containing 1.0% roflumilast, the hair was clipped from the back of each animal. Telazol (3 to 5 mg/kg, IM) was used to sedate the animals for the shaving procedure. Care was taken to avoid abrading the skin. 2 grams of cream for each kg of pig weight was distributed over the clipped skin area by gentle inunction with a glass stirring rod or appropriate instrument (e.g., stainless steel spatula). The cream was applied evenly with a thin, uniform film beginning at the scapular region and moving caudally over the test site. The width of the test site area was bilaterally divided by the spine. Equal numbers of male and female pigs were dosed with 1.0%, 0.5%, 0.3%, or 0.15% roflumilast cream. Blood was sampled from the anterior vena cava through the thoracic inlet or other suitable vein pre-dose (time=0), 1, 2, 4, 8 and 24 hours post dose administration. Lag times were calculated by extrapolating the average 1 hour and 2-hour plasma concentrations to the time point of zero roflumilast concentration in the plasma. For individual animals that had 1-hour plasma assays below the level of quantification (0.2 ng/mL), a value of 0.1 was used if the 2-hour PK time point was above 0.2 ng/mL. If the 2-hour PK time point was below the level of quantification, a value of 0 ng/mL was used for the individual animal to calculate the average. The lag time was less than 1 hour for each of the pH=5.5 roflumilast creams regardless of the concentration of roflumilast.

TABLE 2

| Roflumilast Creams pH = 5.5 | Extrapolated Lag Time | Concentration of Roflumilast in Pig Plasma (ng/mL) | | | | |
|---|---|---|---|---|---|---|
| | | 1 hour | 2 hours | 4 hours | 8 hours | 24 hours |
| 1.0% cream (n = 20) | 55 min | 0.1 | 0.9 | 1.6 | 1.08 | 0.7 |
| 0.5% cream (n = 12) | 47 min | 0.2 | 1.1 | 1.2 | 1.0 | 0.6 |
| 0.3% cream (n = 6) | 38 min | 0.2 | 0.8 | 0.7 | 0.8 | 0.3 |
| 0.15% cream (n = 12) | 47 min | 0.2 | 1.1 | 0.4 | 0.4 | 0.2 |

Example 2

TABLE 3

| PEG Cream | Composition | DES Cream | Composition | DIA Cream | Composition |
|---|---|---|---|---|---|
| Roflumilast | 0.5% w/w | Roflumilast | 0.5% w/w | Roflumilast | 0.5% w/w |
| Caprylic/Capric Triglyceride (Miglyol® 812) | 16% w/w | Diethyl Sebacate | 10% w/w | Diisopropyl Adipate | 15% w/w |
| Glycerol Monostearate | 8% w/w | Light Mineral Oil | 0.7% w/w | POE-7 Cocoyl Glycerides | 13.5% w/w |
| Cremophor A6® Ceteareth-6 Stearyl Alcohol | 4% w/w | Sorbitan Monooleate | 0.1% w/w | Cetyl Alcohol | 5% w/w |
| PEG 400 | 62.5% w/w | Propylene Glycol | 7.5% w/w | Parafin | 1% w/w |

TABLE 3-continued

| PEG Cream | Composition | DES Cream | Composition | DIA Cream | Composition |
|---|---|---|---|---|---|
| Purified Water | q.s. ad 100% | Methylparaben | 0.17% w/w | Lanolin | 2% w/w |
| | | Propylparaben | 0.03% w/w | PEG 400 | 3% w/w |
| | | Edetate Disodium | 0.05% w/w | Methylparaben | 0.2% w/w |
| | | Pemulen TR-1 | 0.4% w/w | Xanthan Gum | 0.3% w/w |
| | | Carbopol 981 | 0.6% w/w | Disodium EDTA | 0.1% w/w |
| | | 1 N NaOH | 3.0% w/w | Solan-75 PA | 3% w/w |
| | | Purified Water | q.s. ad 100% | Purified Water | q.s. ad 100% |

TABLE 4

| 0.05% Roflumilast Cream Components | Composition (%) w/w | | | | |
|---|---|---|---|---|---|
| Roflumilast | 1.0 | 0.15 | 0.5 | 0.5 | 0.5 |
| Petrolatum, USP | 10.0 | 10.0 | 10.0 | 10.0 | 10.0 |
| Isopropyl Palmitate, NF | 5.0 | 5.0 | 5.0 | 5.0 | 5.0 |
| Crodafos CES cetostearyl alcohol dicetyl phosphate ceteth-10 phosphate | 10.0 | 10.0 | 10.0 | 10.0 | 10.0 |
| Diethylene Glycol Monoethyl Ether, NF (Transcutol P) | 25.0 | 25.0 | 25.0 | 25.0 | 25.0 |
| Hexylene Glycol, NF | 2.0 | 2.0 | 2.0 | 2.0 | — |
| Methylparaben, NF | 0.20 | 0.20 | 0.20 | 0.20 | 0.20 |
| Propylparaben, NF | 0.050 | 0.050 | 0.050 | 0.050 | 0.050 |
| 1N NaOH, NF | q.s. ad pH 5.5 | q.s. ad pH 5.5 | q.s. ad pH 5.0 | q.s. ad pH 6.5 | q.s. ad pH 5.5 |
| Purified Water, USP | q.s. ad 100% | q.s. ad 100% | q.s. ad 100% | q.s. ad 100% | q.s. ad 100% |

In vitro skin penetration testing (IVPT) was used to determine how rapidly eight different cream formulations crossed excised human skin. Human cadaver skin was procured from two donors (Caucasian male age=30 abdomen skin dermatomed to an average thickness of 510 μm and Caucasian male age=55 abdomen skin dermatomed to an average thickness of 360 μm). Dermatomed skin was received frozen from a US tissue bank and stored at −20° C. until use. Skin was loaded onto vertical Franz cells having a 0.503 cm$^2$ (8 mm in diameter) diffusion area and a receptor chamber filled with 3.0 ml of 4% BSA in water containing 0.01% gentamicin sulfate thermostated at 32° C. Using a positive displacement pipette, 5 microliters of cream was dosed on each Franz Cell (10 mg per square centimeter of skin). Receptor solutions were analyzed using a validated LC-MS/MS (Kinetex C18, 5 μm, 2.1×50 mm column, Shimadzu LC20ADXR pumps and AB Sciex API 4000 Turbo Spray detector). The cumulative amount of roflumilast assayed in the receptor solution is the average of four replicate IVPT measurements.

As shown in FIG. 3, the five creams containing Crodafos CES as the emulsifier had measurable levels of roflumilast in the receptor solution one hour after dosing. These creams had essentially the same extrapolated lag times in the range of 50-60 minutes, slightly less than 1 hour when adjusted to pH values between 5.0 and 6.5. Removing hexylene glycol from the Crodafos CES cream formulation produced the product with the shortest lag time, i.e. the highest concentration of roflumilast (0.4 ng/mL) at 1 hour. It was concluded that hexylene glycol was not the excipient causing roflumilast to rapidly cross human stratum corneum, i.e. IVPT lag time of less than 1 hour.

The DES, DIA and PEG creams did not transport significant amounts of roflumilast across human skin until three hours after the dose of cream was applied. Two of these three long lag time cream formulations contained methylparaben, one contained both methylparaben and propylparaben. It was concluded that the low levels of methylparaben and propylparaben required to preserve the creams did not shorten the lag time of roflumilast across the skin.

The DES Cream contained light mineral oil and the DIA Cream contained paraffin. Mineral oil is the low molecular weight fraction of petrolatum and paraffin is the high molecular weight fraction of petrolatum. This indicated that the surprisingly short lag times of the Crodafos CES creams was due to either the cream containing Crodafos CES, DEGEE or a combination.

Example 3

TABLE 5

| 0.15% Roflumilast Formulations | Composition (% w/w) | | | |
|---|---|---|---|---|
| | Cream | 10% CES: 25% DEGEE | 10% CES | 25% DEGEE |
| Roflumilast | 0.15 | 0.15 | 0.15 | 0.15 |
| Petrolatum, USP | 10 | — | — | — |
| Isopropyl Palmitate, NF | 5 | — | — | — |
| Crodafos CES cetostearyl alcohol dicetyl phosphate ceteth-10 phosphate | 10 | 10 | 10 | — |
| Diethylene Glycol Monoethyl Ether, NF (Transcutol P) | 25 | 25 | — | 25 |
| Hexylene Glycol, NF | 2 | — | — | — |
| Methylparaben, NF | 0.20 | — | — | — |
| Propylparaben, NF | 0.050 | — | — | — |
| 1N NaOH, NF | q.s. ad pH = 5.5 | q.s. ad pH 4.0 to 8.2 | q.s. ad pH = 6.5 | q.s. ad pH = 6.5 |
| Purified Water, USP | q.s. ad 100% | q.s. ad 100% | q.s. ad 100% | q.s. ad 100% |

Male and female swine (Gottingen Minipig® breed) were ordered to weigh 8 to 12 kg at arrival. On the day prior to administration of topical cream containing 0.15% roflumilast, the hair was clipped from the back of each animal. Telazol (3 to 5 mg/kg, IM) was used to sedate the animals for the shaving procedure. Care was taken to avoid abrading the skin. Two (2) grams of cream for each kg of pig weight was distributed over the clipped skin area by gentle inunction with a glass stirring rod or appropriate instrument (e.g., stainless steel spatula). The cream was applied evenly with a thin, uniform film beginning at the scapular region and moving caudally over the test site. The width of the test site area was bilaterally divided by the spine. Six pigs (3 males and 3 females) were dosed with 0.15% roflumilast topical semisolid products and twelve pigs (6 males and 6 females) were dosed with the 0.15% roflumilast cream. Blood was sampled from the anterior vena cava through the thoracic inlet or other suitable vein pre-dose (time=0), 1, 2, 4, 8 and 24 hours post dose administration. Lag times were calculated by extrapolating the average 1 hour and 2-hour plasma concentrations to the time point of zero roflumilast concentration in the plasma. For individual animals that had 1-hour plasma assays below the level of quantification (0.2 ng/mL), a value of 0.1 was used if the 2-hour PK time point was above 0.2 ng/mL. If the 2-hour PK time point was below the level of quantification, a value of 0 ng/mL was used for the individual animal to calculate the average. The lag time is less than 1 hour for all topical semisolid formulations at pH=6.5 or below and significantly greater than 1 hour for the semisolid having a pH value of 8.2.

TABLE 6

| 0.15% Roflumilast Formulation | pH | Extrapolated Lag Time | Concentration of Roflumilast in Pig Plasma (ng/mL) | | | | |
|---|---|---|---|---|---|---|---|
| | | | 1 hour | 2 hours | 4 hours | 8 hours | 24 hours |
| 10% CES:25% DEGEE | 4.0 | 47 min | 0.2 | 0.4 | 0.4 | 0.3 | 0.1 |
| Cream | 5.5 | 47 min | 0.2 | 1.1 | 0.4 | 0.4 | 0.2 |
| 10% CES:25% DEGEE | 6.5 | <45 min | 0.2 | 0.3 | 0.3 | 0.2 | 0.1 |
| 10% CES | 6.5 | <45 min | 0.2 | 0.4 | 0.3 | 0.1 | 0 |
| 25% DEGEE | 6.5 | 36 min | 0.2 | 0.7 | 0.6 | 0.3 | 0.2 |
| 10% CES:25% DEGEE | 7.5 | <45 min | 0.2 | 0.3 | 0.4 | 0.3 | 0.1 |
| 10% CES:25% DEGEE | 8.2 | >90 min | 0 | 0.1 | 0.2 | 0.1 | 0.1 |

Example 4

A target amount of 480 grams Sterile Water for Irrigation-USP was accurately weighed into a 1000 ml glass beaker and 20 grams of Sodium Hydroxide Pellets-NF was added and mixed using a stir bar until complete dissolution. This solution was set aside and labeled 1 N Sodium Hydroxide.

Target weights pf 1,000 grams White Petrolatum-USP, 500 grams Isopropyl Palmitate-NF, and 1,000 grams of phosphate-ester self-emulsifying wax (CRODAFOS™ CES) was weighed into a 4 L glass beaker and heated on a hot plate to 75° C. to 80° C. while mixing with a propeller mixer. The mixture was labeled Oil Phase and was maintained at 75° C. to 80° C.

To the Main Manufacturing Vessel (a 20 L stainless steel vessel) a target weight of 4,225 grams of Sterile Water for Irrigation-USP and a target weight 300 grams 1 N Sodium Hydroxide was added and heated on a hot plate to 75° C. to 80° C. This was recorded as the Aqueous Phase and was maintained at 75° C. to 80° C.

Target weights of 2,400 grams of Transcutol P-NF, 200 grams of Hexylene Glycol-NF, 20.0 grams of Methylparaben-NF, and 5.0 grams of Propylparaben NF were accurately weighed into a 7 L stainless steel beaker and propeller mixed until a clear homogeneous solution was obtained. Sufficient potency corrected roflumilast (15.2120 grams) was added to this solution to obtain a 0.15% roflumilast cream and this was labeled the API Phase.

The Oil Phase that was maintained at 75° C. to 80° C. was slowly added to the Aqueous Phase maintained at 75° C. to 80° C. in the Main Manufacturing Vessel with homogenizer mixing until a smooth, homogeneous cream was obtained. Using propeller mixing the cream was cooled to 45° C. to 50° C. The API Phase was slowly added to the cream in the main manufacturing vessel and was mixed with the homogenizer. The pH of the finished cream was measured and adjusted to within the pH range of 5.1 to 5.9 using 1 N Sodium Hydroxide or Diluted Hydrochloric Acid, 10% (w/v)-NF. After bulk product release, the cream was filled into aluminum ¾"×3¾" #16 sealed white tubes and the tubes crimped to provide the primary container closure system.

13 human subjects having psoriasis (plaques not covering more than about 5% of the patient's body surface area) treated their skin lesions with the 0.15% Roflumilast cream formulation of example 3. One hour after the first application of topical cream a blood sample was taken, plasma separated and the concentration of roflumilast determined using a validated bioanalytical method. The average plasma concentration of roflumilast for these 13 subjects one hour after the first dose of topical cream was 0.398 ng roflumilast/mL of plasma. The lag time for psoriatic patients applying 0.15% roflumilast cream is less than 1 hour.

Example 5

The same manufacturing process used in Example 4 was performed except sufficient potency corrected roflumilast (50.69 grams) was added to API Phase solution to obtain a 0.5% roflumilast cream.

15 human subjects having psoriasis (plaques not covering more than about 5% of the patient's body surface area) treated their skin lesions with the 0.5% Roflumilast cream formulation of example 2. One hour after the first application of topical cream a blood sample was taken, plasma separated and the concentration of roflumilast determined using a validated bioanalytical method. The average plasma concentration of roflumilast for these 15 subjects one hour after the first dose of topical cream was 0.595 ng roflumilast/mL of plasma. The lag time for psoriatic patients applying 0.5% roflumilast cream is less than 1 hour.

The invention claimed is:
1. A method for reducing roflumilast skin penetration lag time in a patient, comprising topically administering a composition comprising roflumilast diethylene glycol monoethyl ether and an emulsifier blend to said patient, wherein said emulsifier blend comprises cetearyl alcohol, dicetyl phosphate and ceteth-10 phosphate, wherein said composition does not include hexylene glycol, wherein said roflumilast is in an amount of 0.005-2% w/w, and wherein said composition has a pH between 4.0-6.5.

2. The method according to claim 1, wherein said roflumilast skin penetration lag time is less than 60 minutes.

3. The method according to claim 2, wherein said roflumilast skin penetration lag time is less than 45 minutes.

4. The method according to claim 1, wherein said patient is suffering from psoriasis.

5. The method according to claim 1, wherein said patient is suffering from atopic dermatitis.

6. A method for reducing roflumilast skin penetration lag time in a patient, comprising topically administering a composition comprising roflumilast and a) an emulsifier blend comprising cetearyl alcohol, dicetyl phosphate and ceteth-10 phosphate, b) diethylene glycol monoethyl ether, and c) isopropyl palmitate, to a patient in need of such treatment, wherein said composition has a skin penetration lag time of less than 60 minutes, wherein said roflumilast is in an amount of 0.005-2% w/w, wherein said composition has a pH between 4.0-6.5, and wherein said composition does not include hexylene glycol.

\* \* \* \* \*